United States Patent [19]

Newman et al.

[11] Patent Number: 5,091,302

[45] Date of Patent: Feb. 25, 1992

[54] POLYMORPHISM OF HUMAN PLATELET MEMBRANE GLYCOPROTEIN IIIA AND DIAGNOSTIC AND THERAPEUTIC APPLICATIONS THEREOF

[75] Inventors: Peter J. Newman, Shorewood; Richard H. Aster, Milwaukee, both of Wis.

[73] Assignee: The Blood Center of Southeastern Wisconsin, Inc., Milwaukee, Wis.

[21] Appl. No.: 343,827

[22] Filed: Apr. 27, 1989

[51] Int. Cl.$^5$ .................. C12Q 1/68; C07H 15/12; C12N 15/00

[52] U.S. Cl. .......................... 435/6; 536/27; 935/77; 935/78

[58] Field of Search ............... 435/6; 536/27; 935/77, 935/78

[56] References Cited

U.S. PATENT DOCUMENTS

| | | | |
|---|---|---|---|
| 4,351,901 | 9/1982 | Bahl | 435/91 |
| 4,582,788 | 4/1986 | Erlich | 435/6 |
| 4,683,194 | 7/1987 | Saiki | 435/6 |
| 4,683,195 | 7/1987 | Mullis et al. | 435/6 |
| 4,683,195 | 7/1987 | Mullis | 435/6 |
| 4,772,549 | 9/1988 | Frossard | 435/6 |
| 4,800,159 | 1/1989 | Mullis | 435/172.3 |
| 4,801,531 | 1/1989 | Frossard | 435/6 |

FOREIGN PATENT DOCUMENTS

0246864 11/1987 European Pat. Off. .
0258017 3/1988 European Pat. Off. .

OTHER PUBLICATIONS

Maniatis et al, Molecular Cloning: A Laboratory Manual (1982), pp. 230–234.
Lardegren et al, Science, v. 241, pp. 1077–80 (Aug. 1980).
Hickstein et al, Blood 70:89a (1987).
Burk et al, Nucleic Acids Research, vol. 16, N. 14, 1988 p. 7216.
Newman et al, J. Clin. Invest. v. 82, pp. 739–743 (Aug. 1988).
Newman et al., "The Human Platelet Alloantigens PlA1 and PlA2 are associated with a Leucine etc.", J. Clin. Invest. 83:1778–1781 (1989).
Zucker, Scientific American 242:86 (1980).
Keiffer et al, Eur. J. Biochem 164:189 (1987).
Hickstein et al, Blood 70:89a (1987).
Handagama et al., J. Clin. Invest. 86:1364–1368 (1990).
Instructions to Authors J. Clin. Invest.
Newman et al., J. Clin. Invest. 82:73–743 (1988).
Rosa et al., Blood 72(2):593–600 (1988).
Burk et al, Nucleic Acids Research 16(4):7216 (1988).
Newman et al., Arteriosclerosis *(5): 723a–724a (1988).
Maniatis, T. et al; Molecular Cloning: A laboratory Manual (1982); pp. 188–209.
Cardullo, R. A. et al; Detection of Nucleic Acid Hybridization by Nonradiative Fluorescence Resonance Energy Transfer; Proc. Natl. Acad. Sci. USA (Dec. 1988); vol. 85, pp. 8790–8794.
Landegren, U. et al; A Ligase-Mediated Gene Detection Technique; Science (Aug. 1988); vol. 241, pp. 1077–1080.
Newman, P. J. et al; Enzymatic Amplicication of Platelet-Specific Messenger RNA Using the Polymerase Chain Reaction; J. Clin. Invest. (Aug. 1988); vol. 82, 739–743.
Todd, J. A. et al; A Molecular Basis for MHC Class II-Associated Autoimmunity; Science (May 1988); vol. 240, pp. 1003–1009.
Kogan, S. C. et al; An Improved Method for Prenatal Diagnosis of Genetic Diseases by Analysis of Amplified DNA Sequences; The New England Journal of Medicine (Sept. 1987); vol. 317, No. 16, pp. 985–990.
Aster, R. H.; Platelet Antigen Systems.
Phillips, D. R. et al; The Platelet Membrane Glycoprotein IIb–IIIa Complex; The Journal of The American Society of Hematology (Apr. 1988); vol. 71, No. 4, pp. 831–843.
Newman, P. J. et al; The Human Platelet Alloantigens, $PlA^1$ and $PlA^2$, Are Associated with a Leucine$^{33}$/-Proline$^{33}$ Amino Acid Polymorphism in Membrane Glycoprotein IIIa, and Are Distinguishable by DNA Typing; J. Clin. Invest. (May 1989); vol. 83, pp. 1778–1781.

Primary Examiner—Robert A. Wax
Assistant Examiner—Mindy B. Fleisher
Attorney, Agent, or Firm—Foley & Lardner

[57] ABSTRACT

Isolated polynucleotide molecules, and peptides encoded by those molecules, can be used in the analysis of alloantigen phenotypes, as well as in diagnostic and therapeutic applications relating to human platelet $Pl^A$ polymorphism. In this vein, a method for typing blood cell and platelet membrane glycoproteins entails an analysis of amplified cDNA, encoded by platelet and red blood cell mRNA.

26 Claims, 1 Drawing Sheet

POLYMORPHISM OF HUMAN PLATELET MEMBRANE GLYCOPROTEIN IIIA AND DIAGNOSTIC AND THERAPEUTIC APPLICATIONS THEREOF

BACKGROUND OF THE INVENTION

The present invention relates to isolated polynucleotide molecules useful for analyzing alloantigen phenotypes, to peptides encoded by these molecules, and to the diagnostic and therapeutic uses thereof relating to human platelet $Pl^A$ polymorphism, including a method for typing blood cell and platelet membrane glycoproteins which entails an analysis of amplified cDNA encoded by platelet and red blood cell mRNA.

Blood obtained from different individuals has been found to have different antigenic and immune properties, to the extent that antibodies in the blood of one person may react with antigens on red blood cells or platelets in the blood of another individual. These antigens are often found on membrane glycoproteins present on the surface of the cell membranes. These membrane glycoprotein antigens can induce the production of antibodies against them when they are introduced as foreign proteins in transfused blood or in fetal blood. Human platelets and red blood cells contain dozens of identifiable membrane glycoprotein constituents, only some of which have been well characterized.

Membrane glycoproteins which induce antibody production in the same species are called "alloantigens." Alloantigens have been characterized for both red blood cells and platelets. Recognized classes of red blood cell and platelet alloantigens have been described, over the past 30 years, based on observations of antibody reactions occurring when patients have been exposed to blood from other individuals. The lack of sequenceable antigen protein and clonable antigen-encoding mRNA has prevented molecular characterization of the different alleles coding for many clinically important alloantigens.

One system of alloantigens, consisting of the platelet PlAl and PlA2 alloantigens, are carried by the human platelet membrane glycoprotein IIb-IIIa (GPIIb-GPIIIa) complex, which mediates platelet aggregation by providing functional receptors for fibrinogen on platelet surfaces. See Phillips et al., Blood 71: 831-43 (1988). GpIIb and GpIIIa are known to bear a number of clinically important, alloantigenic determinants which are responsible for eliciting an immune response in two well-described clinical syndromes, post-transfusion purpura (PTP) and neonatal alloimmune thrombocytopenia (NATP). See Kunicki & Newman in CURRENT STUDIES IN HEMATOLOGY AND BLOOD TRANSFUSION 18-32 (1986); Aster in ADVANCES IN IMMUNOLOGY AND BONE MARROW TRANSPLANTATION 103-118 (1984).

The alloantigen system most frequently implicated in these disorders is the $Pl^A$ alloantigen system. There are two serologically defined, but molecularly undefined, allelic forms of the $Pl^A$ alloantigen, designated "$Pl^{A1}$" and "$Pl^{A2}$," which are thought to be expression products of the GPIIIa gene. Kunicki & Newman, id., at 18-32. The gene frequencies for these two alleles have been calculated to be 85% for A1 and 15% for A2, see Shulman et al., J. Clin. Invest 40: 1597-620 (1961). Since 98% of the population carries the $Pl^{A1}$ antigen, individuals who are $Pl^{A2}$ homozygotes are at risk of producing anti-$Pl^{A1}$ antibodies against paternally-inherited $Pl^{A1}$ antigens present on fetal platelets, and are most likely to develop PTP following blood transfusion.

Determination of the amino acid sequence variations that are presumably responsible for forming the relevant epitopes of red blood cell and platelet alloantigens has been achieved in only a few instances, due largely to the formidable difficulties in obtaining protein-sequence information from those often large glycoproteins. For example, the amino-acid sequence variation responsible for the relevant epitopes has not yet been reported for either the $Pl^{A1}$ or $Pl^{A2}$ forms of the 100 kilodalton (kd) GPIIIa molecule. In this regard, there is considerable data to support the notion that platelets and red blood cells, since they are anucleate cells, possess only vestigial amounts of protein-synthetic capability, although specific protein biosynthesis has been demonstrated in platelets, see Plow, Thromb. Haemostasis 42: 666-78 (1979); Kieffer et al, Eur. J. Biochem. 164: 189-95 (1987); Belloc et al, Biochim. Biophys. Acta. 925: 218-25 (1987), and in newly formed red cells (reticulocytes). Thus, it has not been considered feasible to obtain platelet or red blood cell cDNA libraries, thereby to analyze alloantigen-encoding sequences and determine the molecular basis of the alloantigen phenotypes.

SUMMARY OF THE INVENTION

It is therefore an object of the present invention to provide DNA molecules that can be used in analyzing an alloantigen phenotype from platelets and red blood cells.

It is also an object of the present invention to provide methodology for typing membrane glycoproteins of human platelet and red blood cells, based on information obtained through the analysis of cDNA discovered to be producible from anucleate-cell (platelet and red blood cell) mRNA.

It is yet another object of the present invention to provide ready means for determining platelet Pl alloantigen phenotypes.

It is still a further object of the present invention to provide polypeptide molecules useful in generating antibodies that distinguish between the alleles of different platelet membrane qlycoproteins Another object of the present invention is to provide methods for diagnosing and treating certain clinical syndromes related to an immune response associated with platelet membrane glycoprotein alloantigens.

In achieving these objects, there has been provided, in accordance with one aspect of the present invention, an isolated DNA molecule that comprises a DNA sequence comprising at least nucleotide 196 of GPIIIa. In a preferred embodiment, nucleotide 196 comprises a cytosine or a thymine base.

In accordance with another aspect of the present invention, a method has been provided for typing human platelet or red blood cell surface membrane glycoproteins, comprising the steps of (A) synthesizing cDNA from human platelet or red blood cell mRNA of a first individual, (B) amplifying the cDNA to produce amplified cDNA and (C) analyzing the amplified cDNA to determine a platelet or red blood cell phenotype. In one preferred embodiment, step (C) comprises
(i) digesting the amplified cDNA with a restriction endonuclease to produce cDNA fragments, the endonuclease recognizing a cleavage site that distinguishes a nucleotide sequence of an allele of a platelet or red blood cell alloantigen from other alleles and (ii) analyzing the cDNA fragments to determine a platelet or red blood cell phenotype. In another preferred embodiment, the cDNA comprises a sequence that is encoded by at least nucleotide 196 of GPIIIa mRNA and the restriction endonuclease recognizes a restriction site, which comprises or is adjacent to a nucleotide sequence that includes nucleotide 196 of GPIIIa.

A method has also been provided, in accordance with still another aspect of the present invention, for typing platelet Pl$^A$ surface membrane glycoproteins comprising the steps of (A) obtaining genomic DNA from a first individual and (B) analyzing the genomic DNA to determine a platelet Pl$^A$ alloantigen phenotype. In a preferred embodiment, step (B) comprises (i) digesting the genomic DNA with a restriction endonuclease to produce DNA fragments, (ii) hybridizing the DNA fragments with a labeled allele-specific oligonucleotide probe that distinguishes a nucleotide sequence of an allele of a platelet Pl$^A$ alloantigen from other alleles and (iii) analyzing the DNA fragments that have hybridized to the probe to determine a platelet PlA phenotype.

According to another aspect of the present invention, a method is provided for typing a platelet Pl$^A$ alloantigen comprising the steps of (A) obtaining genomic DNA from a first individual, (B) amplifying the genomic DNA to produce amplified genomic DNA and (C) analyzing the amplified genomic DNA to determine a platelet Pl$^A$ alloantigen phenotype. Step (C), in one preferred embodiment, comprises (i) hybridizing the amplified genomic DNA with a pair of oligonucleotide probes, wherein a first probe of the pair of probes is labeled with a first probe and a second probe of the pair of probes is labeled with a second probe, such that the first probe is distinctly labeled from the second probe, such that the pair of probes hybridize adjacently to each other at a nucleotide, wherein the nucleotide distinguishes an allele, of a platelet Pl$^A$ alloantigen, from other alleles, (ii) ligating the probes in a ligation reaction to produce ligation products, wherein (a) the first probe becomes ligated to the second probe when adjacent nucleotides of the first and the second probe both hybridize to the amplified genomic DNA or (b) the first probe and the second probe are not ligated and (iii) analyzing the products of the ligation reaction to determine the alloantigen phenotype.

In accordance with another aspect of the present invention, there has been provided polypeptide sequence encoded by a nucleotide sequence comprising a polynucleotide encoding at least amino acid 33 of GPIIIa, that distinguishes platelet membrane glycoprotein Pl$^{A1}$ from Pl$^{A2}$.

There has also been provided, in accordance with still another aspect of this invention, an antibody that binds the Pl$^{A1}$ allele of GPIIIa or the Pl$^{A2}$ allele of GPIIIa, (i) the antibody recognizing a polypeptide molecule encoded by a nucleotide sequence comprising an oligonucleotide encoding at least amino acid 33 of GPIIIa that distinguishes platelet membrane glycoprotein Pl$^{A1}$ from Pl$^{A2}$ and (ii) the antibody binding either the Pl$^{A1}$ form or the Pl$^{A2}$ form.

According to still another aspect of the present invention, a method is provided for treating post-transfusion purpura or neonatal alloimmune thrombocytopenia (NATP), comprising the step of administering to a first individual a formulation comprised of a peptide in a pharmacologically effective concentration and a physiologically-compatible carrier therefor, the first individual suffering from the post-transfusion purpura or the mother of a fetus at risk for developing NATP, and having anti-Pl$^{A1}$ or anti-Pl$^{A2}$ antibodies, wherein the peptide binds an antibody selected anti-Pl$^{A2}$ antibody.

There has also been provided, according to a further aspect of the present invention, a kit for typing platelet Pl$^A$ alloantigens, comprising (a) a receptacle containing a solution of an endonuclease recognizing a cleavage site that distinguishes a nucleotide sequence of an allele of a platelet PlA alloantigen from other alleles, (b) a receptacle containing a solution of a labeled oligonucleotide probe that distinguishes an allele of a platelet Pl$^A$ alloantigen, the allele comprising nucleotide 196 of GPIIIa, from other alleles, (c) a receptacle containing a solution of an antibody that binds a Pl$^{A1}$ antigen or a Pl$^{A2}$ antigen, the antibody (i) recognizing a polypeptide molecule encoded by a nucleotide sequence encoding at least amino acid 33 of GPIIIa and (ii) binding either the Pl$^{A1}$ antigen or the Pl$^{A2}$ antigen.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

Figure 1:
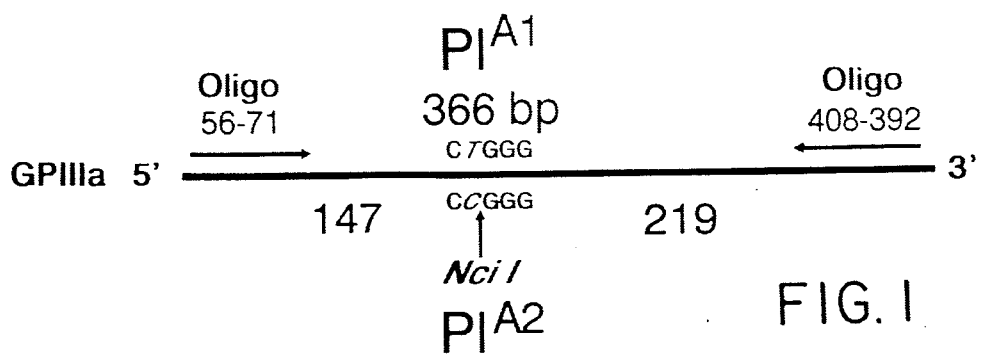
FIG. 1 is diagrammatic representation of the NH$_2$-terminal region of the GPIIIa mRNA molecule. The locations of two oligonucleotide primers used for PcR amplification are also shown, as is the polymorphic sequence at base 196 of the amplified cDNA.

Although the generation of cDNA from platelet or red blood cell mRNA was previously thought to be unfeasible, a new approach has been discovered for examining platelet- and red blood cell-specific mRNA sequences from single individuals. It is been found that mRNA can be obtained from platelets and red blood cells in quantities sufficient for isolation, cDNA generation, and amplification. By generating and amplifying cDNA produced from mRNA of a number of individuals of known red blood cell or platelet allotypes, the nucleotide sequence variations that exist in the genes that express alloantigen determinants can be ascertained. Furthermore, by isolating and amplifying mRNA from a number of individuals of known allotype, it is possible, pursuant to the present invention, to identify phenotype-specific nucleotide sequence variations in corresponding genes.

To obtain amplified cDNA from red blood cell or platelet mRNA, mRNA derived, using conventional methods, see, e.g., MANIATIS ET AL, MOLECULAR CLONING: A LABORATORY MANUAL 187-210 (Cold Spring Harbour Laboratory, 1982), from platelets or red blood cells can be converted to cDNA and then enzymatically amplified to produce microgram quantities of platelet- or red blood cell-specific cDNA. This amplification is preferably accomplished via the "polymerase chain reaction" (PcR) method disclosed by U.S. Pat. Nos. 4,683,195 and 4,800,159, the respective contents of which are hereby incorporated by reference.

More specifically, in the process of generating and amplifying cDNA encoded by the isolated platelet or red blood cell mRNA, oligonucleotide primer pairs can be constructed that allow enzymatic amplification of a segment of an mRNA molecule that encodes an amino-acid sequence defining the polymorphism. The corresponding, isolated cDNAs can then be analyzed to determine the molecular basis of observed phenotypic differences. The ability to compare directly the nucleotide and corresponding amino-acid sequences of genes encoding alleles of alloantigens is made possible by (1) the discovery that cDNA can be generated and amplified successfully from platelet or red blood cell mRNAs and (2) the determination of a nucleotide sequence of an alloantigen which is thought to be polymorphic. As such, this application represents a novel application of the PcR technique heretofore not deemed feasible.

The molecular description of polymorphisms associated with platelet or red blood cell alloantigens can be provided by analyzing amplified cDNA, generated from red blood cell or platelet mRNA, according to one of the following methods: differential restriction endonuclease digestion (DRED), allele-specific oligonucleotide probing (ASOP), and ligase-mediated gene detection (LMGD). Additional methods of analysis would also be useful in this context, such as fluorescence resonance energy transfer (FRET) as disclosed by Wolf et al, *Proc. Nat. Acad. Sci. USA* 85: 8790-94 (1988), the contents of which are hereby incorporated by reference.

DRED analysis is accomplished in the following manner. If conditions occur including (1) a particular amplified cDNA segment contains a sequence variation that distinguishes an allele of a polymorphism and (2) this sequence variation is recognized by a restriction endonuclease, then the cleavage by the enzyme of a particular polynucleotide segment can be used to determine the alloantigen phenotype. In accomplishing this determination, amplified cDNA derived from platelet or red blood cell mRNA is digested and the resulting fragments are analyzed by size. The presence or absence of nucleotide fragments, corresponding to the endonuclease-cleaved fragments, determines which phenotype is present.

For example, cDNA generated from GPIIIA mRNA and a cytosine(C)↔thymidine(T) polymorphism at base 196 is revealed by examination of the nucleotide sequence contained in cDNA generated from mRNA derived from a $Pl^{A2}$ homozygous individual. This single nucleotide substitution results in the creation of a unique restriction enzyme cleavage site for the restriction endonuclease NciI. In this example, utilizing the ability of the restriction endonuclease NciI, to discriminate between these two polymorphic sequences, the phenotypes of individuals can be determined by the above described manner. Then, after further sequence analysis of the resulting restriction fragments, it can be demonstrated that the $Pl^{A2}$ form of GPIIIa mRNA contains the codon CCG (encoding the amino acid proline at position 33), in place of the CUG (which encodes leucine at position 33), present in the $Pl^{A1}$ allele.

In ASOP analysis according to conventional methods, oligonucleotide probes are synthesized that will hybridize, under appropriate annealing conditions, exclusively to a particular amplified cDNA segment that contains a nucleotide sequence that distinguishes one allele from other alleles of a red blood cell or platelet membrane glycoprotein. This specific probe is discernably labeled so that when it hybridizes to the allele distinguishing cDNA segment, it can be detected, and the specific allele is thus identified.

For example, oligonucleotide probes can be synthesized, in accordance with the present invention, that will hybridize to a cDNA segment encoded by GPIIIa mRNA that contains either cytosine or thymidine at nucleotide 196, but not both. These allele-specific probes can then be labeled appropriately and added to the generated cDNA segments under annealing conditions, such that one of the allele-specific probes hybridizes and can be detected. The specific $Pl^{A1}$ or $Pl^{A2}$ allele sequence is thus identified.

In the course of the third method of analysis, LMGD, as disclosed by Landegren et al., *Science* 241: 1077-80 (1988), the contents of which are hereby incorporated by reference, a pair of oligonucleotide probes are synthesized that will hybridize adjacently to each other, i.e., to a cDNA segment under appropriate annealing conditions, at the specific nucleotide that distinguishes one allele from other alleles of a red blood cell or platelet membrane glycoprotein. Each of the pair of specific probes is labeled in a different manner, and when it hybridizes to the allele-distinguishing cDNA segment, both probes can be ligated together by the addition of a ligase.

When the ligated probes are isolated from the cDNA segments, both types of labeling can be observed together, confirming the presence of the allele-specific nucleotide sequence. Where the above- described pair of differently labeled probes bind to a nucleotide sequence containing a distinguishing nucleotide of a different allele, the probe pair is not ligatable and, after the probes are isolated from the cDNA segments, both types of labeling are observed separately.

An exemplary LMGD analysis, according to the present invention, entails the use of a pair of oligonucleotide probes that bind to a cDNA segment adjacently to each other at a nucleotide corresponding to nucleotide 196 of GPIIIa, wherein one probe is radioactively $^{32}P$-labeled and the other probe is biotin-labeled. The biotin labeled probe hybridizes nucleotides 176-196 of GPIIIa, wherein nucleotide 196 contains a cytosine, which distinguishes the $Pl^{A2}$ allele. The $^{32}P$ labeled probe hybridizes nucleotides 197-217 of GPIIIa and, therefore will hybridize adjacently to the biotin labeled probe. These probes are then added under annealing conditions such that they hybridize adjacently to each other spanning nucleotides 176-217 of GPIIIa. When the $Pl^{A2}$ allele sequence is present in the amplified cDNA, then the addition of a ligase will result in the biotin labeled probe being covalently bound to the $^{32}P$- labeled probe. The ligation is possible, because the ends of the probes that are adjacent to each other (hybridized to nucleotides 196 and 197) are both hybridized to the cDNA. In the case where these two probes hybridize to the Pl$^{A1}$ allelic form of the cDNA sequence, the biotin-labeled probe end at nucleotide 196 is not hybridized appropriately, preventing the ligation step from occurring. When this pair of probes binds completely to the Pl$^{A2}$ allele sequence, therefore, the probes are ligated and when the probes are separated from the Pl$^{A2}$ sequence and exposed so as to be detected, both the biotin/strepavidin and the $^{32}$P labeling are present together. When the Pl$^{A1}$ allele sequence is hybridized, on the other hand, the probes cannot be ligated, and the biotin/strepavidin-and $^{32}$P-labeling are observed separately. In this manner, the Pl$^{A1}$ and Pl$^{A2}$ alleles sequences and corresponding phenotype can be distinguished.

Alternatively, DRED, ASOP and LMGD or other suitable methods of analysis, such as FRET, can be used with genomic or amplified-genomic DNA to distinguish platelet membrane glycoprotein Pl$^{A1}$ from Pl$^{A2}$, starting with any nucleated cell sample, obtained from an individual, from which DNA can be isolated in sufficient quantities for analysis. Amplified genomic DNA would be amplified from isolated genomic DNA in the same manner as described above for cDNA. Once a tissue sample, such as cells scraped from the inside of an individual's cheek, has been obtained, genomic DNA isolated by conventional procedures can be analyzed directly per se or amplified prior to analysis.

The foregoing description of the three types of analysis would apply to the use of genomic DNA or amplified-genomic DNA, with the term "cDNA" being replaced with "genomic or amplified genomic DNA." One difference in the analysis of genomic DNA or amplified genomic DNA is that the GPIIIa sequence used for designing a suitable oligonucleotide probe would have to include any intronic sequences, which would not be present in the cDNA of GPIIIa, that were near or adjacent to the nucleotide that determines the Pl$^A$ phenotype.

The presence of intronic sequences near the phenotype-determining nucleotide can be determined by sequence analysis of genomic DNA, accomplished via Maxam-Gilbert or another conventional technique. Sequence-analysis data which indicate that an intron is near the phenotype-determining nucleotide can be used to design oligonucleotides that span the intron/exon boundary, so that a Pl$^A$ phenotype can be ascertained.

For example, sequence analysis conducted by Dr. Gilbert C. White II, University of North Carolina, (Chapel Hill, NC), has shown that an 800-nucleotide intron is located between bases 185 and 186 of the GPIIIa cDNA (personal communication of unpublished results). A nucleotide sequence is set out below which includes the intron/exon boundary and which is relevant to the design of a suitable, Pl$^A$ phenotype-determining oligonucleotide probe:

5,'-tttgggctcctgtcttacag/GCCCTGCCT-3,'

In this sequence, the lower case letters represent the intronic sequence and the upper case letters represent the cDNA sequence. The line represents the intron/exon boundary.

The ability to perform DNA-typing analysis for determination of Pl$^A$ phenotypes, pursuant to the present invention, has a number of useful clinical applications, including but not limited to those involving determination of an alloantigen phenotype of an individual, and the diagnosis and treatment of a pathological immune response (or potential response) involving foreign alloantigens or antibodies. In accordance with the present invention, alloantigen phenotyping is effected by generating amplified cDNA from red blood cell or platelet mRNA, which permits diagnosis of individuals for the purpose of treating or preventing pathological immune responses. Once the nucleotide-sequence variations specific for each allelic form of the alloantigens of a given class are determined, other conventional methods can be employed, through the use of genomic DNA or platelet RNA, to perform the same type of diagnosis on other individuals. These methods would include, but are not limited to, allele-specific nucleotide probing and ligase-mediated gene detection, as previously described.

Diagnostic kits can also be used, in accordance with the present invention, for the determination and diagnosis of alloantigen phenotypes via the procedures described herein. Such a kit can include, inter alia, antibodies to alloantigens expressed by the above-described Pl$^{A1}$- and Pl$^{A2}$-encoding sequences, which antibodies would react with the blood sample of an individual so as to indicate whether that individual has a Pl$^{A1}$ or Pl$^{A2}$ phenotype. Alternatively, all the reagents required for the detection of nucleotide(s) that distinguish the Pl$^A$ alloantigens, by means described herein, can be provided in a single kit that uses isolated genomic DNA or platelet mRNA from an individual. Such a kit, containing a restriction endonuclease and/or a labeled probe that distinguish nucleotide 196 of GPIIIa, can be utilized for Pl$^A$ alloantigen phenotyping.

A further beneficial use of the nucleotide sequences that distinguish the Pl$^{A1}$ allele from the Pl$^{A2}$ allele is to obtain or synthesize the respective expression product, in the form of a peptide, encoded by these nucleotide sequences. These peptides can be used to generate antibodies for diagnostic and therapeutic uses, for example, with regard to pathological conditions such as PTP or NATP.

In this context, the term "antibodies" is used to denote, inter alia, monoclonal or polyclonal antibodies, specific for peptides generated from nucleotide sequences distinguishing either Pl$^{A1}$ or Pl$^{A2}$ alleles, that can be generated by injecting a peptide into mice or other suitable laboratory animal. In the case of monoclonal antibody production, one proceeds by isolating lymphocytes and fusing them with myeloma cells, producing hybridomas. The cloned hybridomas are then screened for production of antibodies specific for sequences that are diagnostic of the Pl$^{A1}$ or Pl$^{A2}$ form of the GPIIIa membrane glycoprotein. In addition, the term "antibodies" encompasses fragments, like Fab and F(ab')$_2$, of anti-Pl$^{A1}$ or anti-Pl$^{A2}$ antibodies, and conjugates of such fragments, and so-called "antigen binding proteins" (single-chain antibodies) based on anti-Pl$^{A1}$ or anti-Pl$^{A2}$ antibodies, in accordance, for example, with U.S. Pat. No. 4,704,692, the contents of which are hereby incorporated by reference. Human alloantisera currently used for serological typing are specifically excluded from this definition.

Diagnostic applications of these antibodies are exemplified, according to the present invention, by the use of a kit containing anti-Pl$^{A1}$ or anti-Pl$^{A2}$ antibodies which undergo a reaction with a sample of an individual's blood to determine a Pl$^{A1}$ or Pl$^{A2}$ platelet phenotype.

Such a reaction involves the binding of anti-Pl$^{A1}$ antibodies to Pl$^{A1}$ antigens or the binding of of antibody-antigen complexes in a blood sample would indicate a positive result. A kit of this sort could be used to diagnose, or to help prevent, the occurrence of pathological conditions like PTP or NATP.

Therapeutic applications for the peptides encoded by these Pl$^{A1}$/Pl$^{A2}$-distinguishing nucleotide sequences, and the corresponding anti-Pl$^{A1}$ or anti-Pl$^{A2}$ antibodies, include their use in the generation, via conventional methods, of antiidiotypic antibodies (that is, "anti-" anti-Pl$^{A1}$ or anti-Pl$^{A2}$ antibodies) such as from hybridomas, as described above. See, for example, U.S. Pat. No. 4,699,880, the contents of which are hereby incorporated by reference. Such antiidiotypic antibodies would bind endogenous or foreign anti-Pl$^A$ antibodies in the blood of an individual, thereby to treat or prevent pathological conditions associated with an immune response to a "foreign" Pl$^A$ alloantigen.

The present invention is further described below by reference to the following, illustrative examples. Used in the examples were plasma samples from ten homozygous Pl$^{A1}$ individuals, five homozygous Pl$^{A2}$ individuals, and three individuals who were heterozygous for the Pl$^A$ allotype. The respective phenotypes of all the test subjects had been identified using well-characterized anti-Pl$^{A1}$ and anti-Pl$^{A2}$ human alloantisera.

EXAMPLE 1

Amplification of Platelet mRNA

In order to examine the amino terminal region of the Pl$^{A2}$ allele, the polymerase chain reaction was used to amplify a 366 base pair (bp) region near the 5, end of platelet GPIIIa mRNA. Human platelets were isolated from whole blood as previously described (Newman et al., *Blood* 69:668-676 (1987)). Briefly, 50 ml of venous blood collected from healthy volunteer donors was anticoagulated with 7 ml of acid citrate dexrose (National Institutes of Health, Formula A), and PGE$_1$ was added to a final concentration of 50 nmol/liter. Platelet-rich plasma (PRP) was prepared by differential centrifugation, and the platelets present in the upper half of the PRP were harvested and washed an additional two times in wash buffer (100 mmol/liter NaCl, 8.5 mmol/liter Tris, 8.5 mmol/liter glucose, and 1 mmol/liter Na$_2$EDTA, pH 7.4). By carefully avoiding the lower half o the PRP, consistent achievement of a platelet/leukocyte ratio of at least 3000:1 was attained. The final paltelet pellet was solubilized in 3.3 ml of buffer composed of 4 mol/liter guanidinium isothiocyanate, 5 mmol/liter sodium citrate, 0.1 mol/liter 2-mercaptoethanol, 0.5% SARKOSYL, 0.1% ANTIFOAM A, and 40 U/ml placental RNAse inhibitor, layered onto a 1.2 ml cushion of 5.7 mol/liter CsCl, and centrifuged at 20° C. in a Ti50.1 rotor at 35,000 rpm for 16 hours (Beckman Instruments, Inc., Fullerton, Calif.). The nearly invisible RNA pellet was resuspended in buffer made up of 10 mmol/liter Tris, 5 mmol/liter EDTA, and 1% SDS, Ph 7.4), extracted with chloroform/butanol, and ethanol precipitated essentially as described by Maniatis et al., loc. cit. The resulting purified total platelet RNA fraction recovered using this technique was <1 µg per individual, and was used in all subsequent steps without further fractionation. Our amplification strategy employed 2 sets of oligonucleotide primers, one nested internally to the first. Nested primers are not always necessary.

Two pairs of primers were constructed; an outer pair (Primers 1 and 3), and an internally nested pair (Primers 2 and 4) and used to amplify a region of the GPIIIa mRNA molecule that encodes the amino terminus of mature glycoprotein IIIa. Primer (5'-CGCGGGAGGCGGACGAGATGCG-3') corresponds to the RNA strand from bases 4-25 of the published nucleotide sequence (Fitzgerald et al., *J. Biol. Chem.* 262: 3936-3939, 987). Primer 2 (5'-GACTCGAGACTGTGCTGGCGCTG-3') corresponds to bases 56-71 of the RNA strand, with an additional 7 bp encompassing an Xho I restriction enzyme recognition site incorporated onto the 5'-end to facilitate subsequent subcloning into plasmid vectors. The two anti-sense oligonucleotides were Primer 3 (5'-CGCACTTGGATGGAGAAATTC-3'), which corresponds to nucleotides 4 12-392, and Primer 4 (5'-CCGGATCCTTGGATGGAGAAATTC-3'), which corresponds to bases 408-392 plus an additional 7 base pairs that contain a Bam HI site. Primer 3 was used to prime first strand cDNA synthesis, using platelet mRNA as a template, in a total volume of 50 µl as previously described, id. Newman et al (1988). All ensuing PcR reactions Were performed in a programmable DNA Thermal Cycler (Perkin-Elmer Cetus Corp., Norwalk, Conn.).

The first 10 rounds of PcR were performed using Primers 1 and 3 in a total volume of 100 µl using a regimen consisting of denaturing polynucleotide strands at 94° C. for 90 sec., annealing primers at 37° C. for 2 min, and primer extending with Taq polymerase (Perkin-Elmer Cetus Corp.) at 72° C. for 3.5 minutes. Following the fifth thermal cycle, the primer annealing temperature was increased to 42° C. After the tenth cycle, the first primer pair was removed by centrifuge-driven dialysis of the PcR reaction mixture into a nearly identical buffer using Centricon 30 microconcentrators (Amicon Corp, Danvers, Mass.). The first 10 thermal cycles of the PcR amplified bases 4-412 approximately one-thousand fold, and provided a sufficient quantity of GPIIIa-specific cDNA to permit more stringent conditions to be used in subsequent rounds.

The second reaction mix was identical to the first, except that internally nested Primers 2 and 4 were used in place of Primers and 3. Following oligonucleotide exchange, the reaction volume was again brought to 100 µl including 2.5 units of fresh Taq polymerase, and PcR continued for an additional 21 thermal cycles. Primer annealing was performed at 42° C. for rounds 11-15; 47° C. for rounds 16-20, and 55° C. for rounds 21-31. It was found that these conditions maximized specificity and yield for amplification of this particular cDNA. The presence of the additional bases used to form the restriction enzyme sites at the 5' ends of Primers 2 and 4 had no detrimental effect on the quantity of specific DNA produced during the PcR. The remaining thermal cycles amplified bases 56-408 using an internally nested primer pair, which are graphically depicted in the top portion of FIG. 1. This region encodes the first 103 amino acids of the mature GPIIIa protein, as well as a majority of the signal peptide. Using this protocol, we produced microgram amounts of the expected 366 bp cDNA from a number of individuals of known Pl$^A$ phenotype.

EXAMPLE 2

Sequence Analysis of Amplified cDNAs

Figure 2:
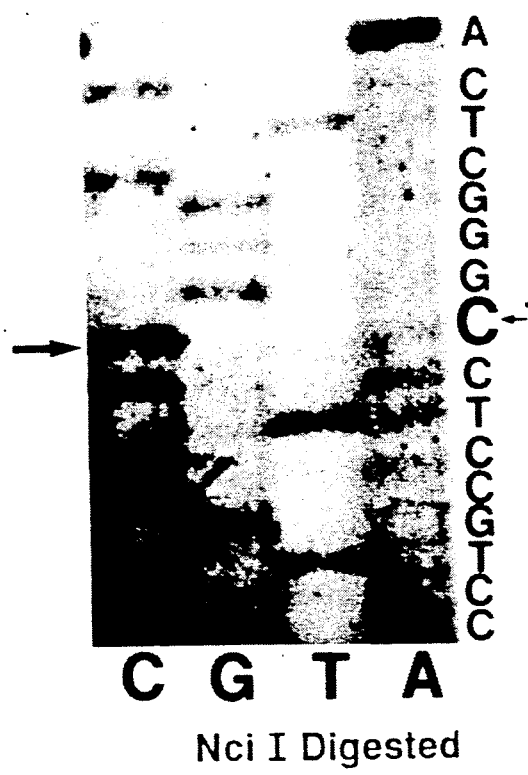
FIG. 2 is a autoradiograph of an electrophoretic gel used in the sequence analysis of amplified GPIIIa cDNA, derived from a Pl$^{A2}$ homozygous individual. A segment of the autoradiograph, encompassing bases 188-203, is shown. A single base substitution of a cytosine (C) (Pl$^{A2}$ allele) for a thymidine (T) (Pl$^{A1}$ allele) at base 196 is indicated with an arrow.

Selected amplified cDNA's were subcloned into the plasmid vector pGEM-7Zf (Promega Biotech, Madison, Wis.), and subjected to nucleotide sequence analysis. Dideoxy-sequencing was performed using the modified T7 phage DNA polymerase, Sequenase™ (United States Biochemicals, Cleveland, Ohio), according to the manufacturer's directions. The complete nucleotide sequence of bases 79–408 from one $Pl^{A2}$ homozygous individual was determined on both strands, and found to be identical to the 3 previously reported sequences for GPIIIa, except at base 196 (sequence numbering according to reference #6), which had a deoxycytosine (C) in place of a deoxythymidine (T). Sequence analysis of 2 different sub-clones of the 366 bp $Pl^{A2}$-derived cDNA product showed the same base substitution, making it unlikely that this nucleotide difference was an artifact generated in vitro during either the reverse transcriptase or Taq polymerase reactions. This single base change (shown in FIG. 2) results in substitution of a Proline for Leucine at amino acid residue 33 of the mature GPIIIa molecule, and is likely to impart significant secondary structural differences in the polypeptide chain.

EXAMPLE 3

Restriction Enzyme Analysis of GPIIIa Allotypes.

Analysis of the GPIIIa sequence from bases 56–408 revealed that substitution of a C for a T at base 196 would create a recognition site for the restriction enzyme NciI, which cleaves at 5'-CCGGG-3', but not 5'-CTGGG-3' sequences. To determine whether the thymidine (T)→cytosine (C) substitution found in the $Pl^{A2}$ individual studied above was related to $Pl^A$ allotype, or merely represented an unrelated polymorphism of GPIIIa, platelet RNA was prepared from a total of 18 individuals of known $Pl^A$ phenotype, and then amplified using PcR to yield the same 366 bp product. As illustrated in FIG. 1, NciI should not be able to cleave the 366 bp cDNA from a $Pl^{A1}$ homozygous individual, whereas 2 fragments of 147 and 219 bp would be generated in a $Pl^{A2}$ homozygote.

Figure 3:
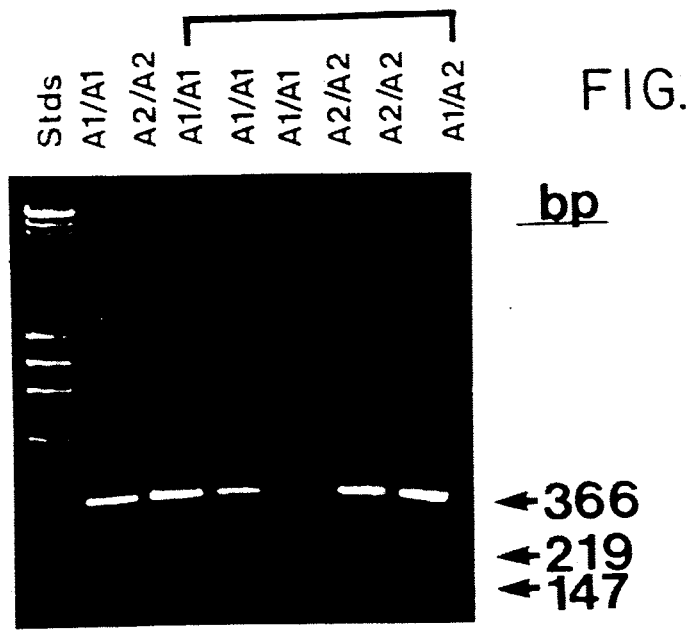
FIG. 3 is a photograph of an electrophoretic gel generated in the course of analyzing Pl$^A$ phenotype by restriction endonuclease digestion, in accordance with the present invention. Bases 56-408 were enzymatically amplified from platelet RNA from eighteen individuals of known Pl$^A$ phenotype. The results from three representative individuals of each possible phenotype are shown on this gel. Heterozygotes for the allele show three bands, corresponding to undigested (Pl$^{A1}$-derived) and cleaved (Pl$^{A2}$-derived) GPIIIa cDNA.

Most PcR reaction products were directly excnanged into sterile water using Centricon 30 microconcentrators, and then digested with NciI (purchased from either New England Biolabs, Beverly, Mass., or Bethesda Research Laboratories, Gaithersburg, Md.). Restriction digests were analyzed on 1.5% agarose gels. Computer analyses of protein and polynucleotide sequences were performed using the program PC/GENE (Intelligenetics Inc . Mountain View, Calif.) operating on an IBM PC/AT-compatible personal computer. FIG. 3 shows that the 366bp cDNA amplified from $Pl^{A1}$ homozygous individuals was not cleaved by NciI, whereas the predicted 219- and 147-bp restriction fragments were obtained from $Pl^{A2/A2}$-derived cDNA. Serologically-determined heterozygotes for the $Pl^A$ phenotype, containing both the $Pl^{A1}$ and $Pl^{A2}$ cDNA sequences, yielded both uncut, 366-bp cDNA and the 219- and 147-bp restriction fragments.

The DNA-typing procedure of the present invention, as described above, predicted the phenotype of ten $Pl^{A1/A1}$, three $Pl^{A1/A2}$, and five $Pl^{A1/A2}$ individuals ($p = 3.8 \times 10^{-6}$).

What is claimed is:

1. A method of typing human platelet glycoproteins, comprising the steps of
    (a) synthesizing cDNA from human platelet;
    (b) amplifying said cDNA to produce amplified cDNA; and then
    (c) analyzing said amplified cDNA to determine a paltelet phenotype.

2. A method as claimed in claim 1, further comprising the step of synthesizing cDNA from human platelet of a second individual, and then repeating steps (b) and (c) on the cDNA of said second individual; and thereafter discriminating between said first and second individuals based on said alloantigen phenotype.

3. A method as claimed in claim 1, wherein step (c) comprises the steps of (i) digesting said amplified cDNA wtih a restriction endonuclease recognizing a cleavage site that distinguishes a nucleotide sequence of an allele, of a platelet alloantigen, from other alleles; and analyzing said cDNA fragments to determine a platelet phenotype.

4. A method as claimed in cailm 3 wherein (i) said cDNA comprises a sequence that encodes at least nucleotide 196 of CPIIIa mRNA and (ii) said restriction endonuclease recognizes a restriction site, which comprises or is adjacent to a nucleotide sequence that includes nucleotide 196 of CPIIIa mRNA.

5. A method as claimed in claim 1, wherein step (c) comprises the steps of (i) hydridizing said cDNA fragments with a labeled allele-specific oligonucleotide probe that distinguishes a nucleotide sequence of a $Pl^A$ allele from another $Pl^A$ allele; and then (ii) analyzing said probe that has hybridized to said cDNA fragments to determine said $Pl^A$ alloantigen phenotype.

6. A method as claimed in claim 5, wherein said $Pl^A$ allele comprises a sequence that is encoded by at least nucleotide 196 of CPIIIa mRNA and said labeled oligonucleotide probe hybridizes to a nucleotide sequence which comprises or is adjacent to nucleotide 196 of GPIIIa mRNA.

7. A method as claimed in claim 1, wherein step (c) comprises the steps of
    (i) hybridizing said amplified cDNA with a pair of oligonucleotide probes to produce a construct, wherein a first probe of said pair is labeled with a first label and a second probe of said pair is labeled with a second label, such that the first label is distinguishable from the second lable, and the probes hydbridize adjacent to each other at a nucleotide that distinguishes a first $Pl^A$ allele from another $Pl^A$ allele; thereafter
    (ii) reacting said construct with a ligase in a reaction medium; and then
    (iii) analyzing said reaction medium to detect the presence of a ligation product comprising said first probe and said second probe.

8. A method as claimed in claim 7, wherein said $Pl^A$ allele comprises a sequence that is encoded by at least nucleotide 196 of GPIIIa mRNA and said labeled oligonucleotide probes hybridize a nucleotide sequence which comprsies or is adjacent to nucleotide 196 of GPIIIa mRNA.

9. A method of typing platelet $Pl^A$ membrane glycoproteins comprising the steps of (a) obtaining genomic DNA from a first individual and (b) analyzing said genomic DNA to determine a platelet $Pl^A$ alioantigen phenotype.

10. A method as claimed in claim 9, further comprising the step of obtaining genomic DNA from a second individual, and then repeating step (b) on the genomic DNA of said second individual; and thereafter discriminating between said first and second individuals based on said Pl$^A$ alloantigen phenotype.

11. A method as claimed in claim 9, whrein step (b) comprises the steps of (i) digesting said genomic DNA with a restriction endonuclease to produce DNA fragments, said endonuclease recognizing a cleavage site that distinguishes a nucleotide sequence of a first Pl$^A$ allele from that of another Pl$^A$ allele; and then (ii) analyzing said DNA fragments with a labeled probe to determine said Pl$^A$ alloantigen phenotype.

12. A method as claimed in claim 11, wherein said Pl$^A$ allele comprises a sequence that is encoded by at least nucleotide 196 of GPIIIa mRNA and said restriction endonuclease recognizes a restriction site which comprises or is adjacent to a nucleotide sequence that includes nucleotide 196 of GPIIIa mRNA.

13. A method as claimed in claim 9, wherein step (b) comprises the steps of (i) digesting said genomic DNA with a restriction endonuclease to produce DNA fragments; thereafter (ii) hybridizing said DNA fragments with a labeled allele-specific oligonucleotide probe that distinguishes a nucleotide sequence of an allele of a platelet Pl$^A$ alloantigen from other alleles; and then (iii) analyzing said probe that has hybridized to said DNA fragments to determine said Pl$^A$ alloantigen phenotype.

14. A method as claimed in claim 13, wherein said Pl$^A$ allele comprises a sequence that is encoded by at least nucleotide 196 of GPIIIa mRNA and said labeled oligonucleotide probe hybridizes to a nucleotide sequence which comprises or is adjacent to nucleotide 196 of GPIIIa mRNA.

15. A method as claimed in claim 9, wherein step (b) comprises the steps of (i) hybridizing said genomic DNA with a pair of oligonucleotide probes to produce a construct, wherein a first probe of said pair is labeled with a first label and a second probe of said pair is labeled with a second labe, such that the first label is distinguishable from the second label, and the pair of probes hybridize adjacently to each other at a nucleotide of said genomic DNA that distinguishes a Pl$^A$ allele from another Pl$^A$ allele; thereafter (ii) reacting said construct with a ligase in a reaction medium; and then (iii) analyzing said reaction medium to detect the presence of a ligation product comprising said first probe and said second probe.

16. A method as claimed in claim 15, wherein said Pl$^A$ allele comprises a sequence that is encoded by at least nucleotide 196 of GPIIIa mRNA and said labeled oligonucleotide probes hybridize to a nucleotide sequence which comprises or is adjacent to nucleotide 196 of GPIIIa mRNA.

17. A method of typing platelets with respect to GPIIIA comprising the steps of (a) obtaining genomic DNA from an first individual, (b) amplifying said genomic DNA to produce amplified genomic DNA and (c) analyzing said amplified genomic DNA to determine a platelet Pl$^A$ alloantigen phenotype.

18. A method as claimed in claim 17, further comprising the step of obtaining genomic DNA from a second individual, and then repeating steps (b) and (c) on the genomic DNA of said second individual; and thereafter discriminating between said first and second individuals based on said alloantigen phenotype.

19. A method as claimed in claim 17, wherein step (c) comprises the steps of (i) digesting said amplified genomic DNA with a restriction endonuclease to produce DNA fragments, said endonuclease recognizing a cleavage site that distinguishes a nucleotide sequence of a first Pl$^A$ allele fro mthat of another Pl$^A$ allele; and thereafter (ii) analyzing said DNA fragments to determine said alloantigen phenotype.

20. A method as claimed in claim 17, wherein step (c) comprises the steps of (i) hybridizing said amplified genomic DNA with a labeled allele-specific oligonucleotide probe that distinguishes a nucleotide sequence of a Pl$^A$ allele from that of another Pl$^A$ allele; and then (ii) analyzing said probe that has hybridized to said amplified genomic DNA to determine said alloantigen phenotype.

21. A method as claimed in claim 20, wherein said Pl$^A$ allele comprises a sequence that is encoded by at least nucleotide 196 of GPIIIa mRNA and said labeled oligonucleotide probe hybridizes to a nucleotide sequence which comprises or is adjacent to nucleotide 196 of GPIIIa mRNA.

22. A method as claimed in claim 17, wherein step (c) comprises the steps of (i) hybridizing said amplified genomic DNA with a pair of oligonucleotide probes to form a construct, wherein a first probe of said pair is labeled with a first label and a second probe of said pair is labeled with a second label, such that the first label is distinguishable from the second label, and the probes hybridize adjacently to each other at a nucleotide that distinguishes a Pl$^{A1}$ allele from another a Pl$^{A2}$ allele; thereafter (ii) reacting said construct with a ligase in a reaction medium; and then (iii) analyzing said reaction medium to detect the presence of a ligation product comprising said first probe and said second probe.

23. A method as claimed in claim 19, wherein said Pl$^A$ allele comprises a sequence that is encoded by at least nucleotide 196 of GPIIIA mRNA and said labeled oligonucleotide probe hybridizes to a nucleotide sequence, which comprises or is adjacent to nucleotide 196 of GPIIIA mRNA.

24. A kit for typing platelet Pl$^A$ alloantigens, comprising
 (a) means for amplifying DNA that comprises at least a portion of a GPIIIA gene or GPIIIA cDNA, wherein said portion includes a nucleotide corresponding to nucleotide 196 of said GPIIIA cDNA, and at least one component selected from the group consisting of
 (b) a receptacle containing a solution of a labeled oligonucleotide probe that distinguishes a Pl$^A$ allele from another Pl$^A$ allele, and
 (c) a receptacle containing a solution of an endonuclease recognizing a cleavage site that distinguishes a nucleotide sequence of a Pl$^A$ allele from another Pl$^A$ alleles.

25. A kit for typing platelet Pl$^A$ alloantigens, comprising a receptacle containing a solution of an antibody that discriminately binds alloantigens expressed by a Pl$^{A1}$ allele or a Pl$^{A2}$ allele of GPIIIA, said antibody (i) recognizing a peptide molecule encoded by a nucleotide sequence encoding at least amino acid 33 of GPIIIA and (ii) binding either said Pl$^{A1}$ allele or said Pl$^{A2}$ allele of GPIIIA.

26. A method as claimed in claim 22, wherein said Pl$^A$ allele comprises a sequence that is encoded by at least nucleotide 196 of GPIIIa mRNA and said labeled oligonucleotide probe hybridizes to a nucleotide sequence which comprises or is adjacent to nucleotide 196 of GPIIIa mRNA.

* * * * *